United States Patent [19]

Naser

[11] 4,233,979
[45] Nov. 18, 1980

[54] METHOD OF SCREWING AN ADAPTER INTO THE HUMAN CRANIUM

[75] Inventor: Georg Naser, Zirndorf, Fed. Rep. of Germany

[73] Assignee: Siemens Aktiengesellschaft, Berlin & Munich, Fed. Rep. of Germany

[21] Appl. No.: 898,486

[22] Filed: Apr. 20, 1978

[30] Foreign Application Priority Data

May 6, 1977 [DE] Fed. Rep. of Germany ....... 2720455

[51] Int. Cl.³ .............................................. A61B 17/00
[52] U.S. Cl. .................................. 128/303 R; 128/310
[58] Field of Search .................... 128/2 S, 310, 303 B, 128/2 P, 303 R, 774, 753; 33/169 B, 174 D

[56] References Cited

U.S. PATENT DOCUMENTS

| | | | |
|---|---|---|---|
| 1,327,114 | 1/1920 | Rhein | 33/169 B |
| 2,663,944 | 12/1953 | Rumbaugh | 33/169 B |
| 4,026,276 | 5/1977 | Chubbuck | 128/2 P |
| 4,121,572 | 10/1978 | Krzeminski | 33/169 B |

Primary Examiner—Robert W. Michell
Assistant Examiner—Michael H. Thaler
Attorney, Agent, or Firm—Hill, Van Santen, Steadman, Chiara & Simpson

[57] ABSTRACT

In an illustrated embodiment a hollow tube is drivingly engageable with the adapter which is to be screwed into place in a pre-formed bore in the cranium. A pin reciprocal within the tube has an abutment gauge at its proximal end which is advanced into engagement with the dura mater. A marking system referenced to the pin visually exhibits the progress of the adapter as it is moved into coplanar relation to the abutment gauge. For example the distal end of the pin may reach a position flush with a surface at the distal end of the assembly when the adapter is in the desired exact final position. As another example the hollow tube may have slots therein exposing a mark on the pin so as to visually indicate the progress of the adapter; specifically a transverse element through the pin which may be manually engaged to advance the abutment, may be observed as an index point relative to markings adjacent the slot on the tube.

1 Claim, 4 Drawing Figures

METHOD OF SCREWING AN ADAPTER INTO THE HUMAN CRANIUM

BACKGROUND OF THE INVENTION

The invention relates to an instrument for screwing into the human skull an adapter which is intended to hold a pressure converter or a similar object, consisting of a pivot pin assembly with a screw grip which is connectible in a force-locking manner to the adapter.

In addition to cerebrospinal pressure measurement in the lateral ventricle via a catheter with an external pressure converter, methods for cerebral pressure measurement have succeeded in which commercial miniature pressure converters are implanted in the epidural skull cavity. In these methods it is important that the pressure sensitive membrane of the pressure receptor rests on the 'dura mater' in a coplanar manner. An adapter which is screwable into the patient's skull to hold and position the pressure converter must be flush with the underside of the bone and must be sealed off from the environment. Adapters of this type are screwed into a prepared bore in the skull by means of an instrument. The instrument generally takes the form of a box spanner which can be connected to the adapter screw in a form and force locking manner by a transverse pin or a polygon profile at the proximal end. Since the thickness of the cranium bone can vary in different patients, the required screw-in depth of the adapter must generally be matched to the individual bone thickness. It is also desirable to control the screw-in depth, i.e. the distance of the proximal adapter surface from the underside of the bone, during the screwing-in operation.

SUMMARY OF THE INVENTION

The object of the invention is to specify an instrument for screwing an adapter into the human skull which renders possible a particularly simple to manage depth control during the screwing-in operation.

According to the invention, the object is achieved by the fact that the pivot pin is a hollow tube having in its interior an axially displaceable element which has an abutment member on the adapter side end for abutment against the 'dura mater' and which, together with the hollow tube, has adjustment marks visible from the outside by which, during a relative axial displacement of the hollow tube and the element when a screwing-in operation of the adapter and pivot pin takes place, the size of displacement is controllable, visibly from the outside. The adjustment marks which are visible externally are preferably formed by the end, facing away from the adapter, of the axially displaceable element and a window shoulder on the top end of the hollow tube. In a special development, the adjustment marks may also be formed by depth indication marks on the axially displaceable element and with recesses on the shaft periphery designed as a window for the depth indication marks. At the same time, means for handling and/or displacement limitation of the axially displaceable element may be disposed in such recesses. The axially displaceable element is preferably a pin guided in the interior of the hollow body, whose end facing away from the abutment member seals flush with the window shoulder of the top end of the hollow tube when the abutment surface of the abutment member and the lower surface of the adapter lie in one plane. The abutment member is formed by a flat disc at the end of the pin which has the same diameter as the external diameter of the hollow tube.

In the instrument according to the invention, the pivot pin with the axially displaceable element forms a compact structural element the handling of which is particularly simple. Further measuring instruments, such as separate depth gauges and similar devices, are thereby made superfluous. The instrument according to the invention now makes exact screwing-in of the adapter into the cranial bone possible in a single operation. The adapter is connected to the instrument in a force locking manner and is applied on the prepared skull opening which has a slightly smaller diameter than the adapter which adapter in the screwing-in operation is self-tapping. The axially displaceable element is displaced in proximal direction until the abutment surface of the abutment member lies coplanar with the 'dura mater'. The axially displaceable element does not alter its position during the screwing-in operation. The actual screw-in depth can be controlled visibly from the outside by the relative displacement of the adjustment marks on the exterior hollow body and the interior axially displaceable element of the instrument and the final position at which the adapter seals flush with the underside of the skull bone be determined.

Further advantages of the invention emerge from the following description of the figures of an embodiment with reference to the accompanying sheets of drawings in conjunction with further subclaims; and other objects, features and advantages will be apparent from this detailed disclosure and from the appended claims.

BRIEF DESCRIPTION OF THE DRAWINGS

FIG. 1a is a partial elevational view of the instrument as seen in the direction of the arrrow Ia of FIG. 1;

FIG. 2 shows a longitudinal section, corresponding to FIG. 1, of the screwing-in instrument connected to the adapter at the beginning of the application; and FIG. 2a shows a partial elevational view of the instrument as seen in the direction of arrow IIa in FIG. 2 and corresponding to FIG. 1a.

DETAILED DESCRIPTION

Figure 1:
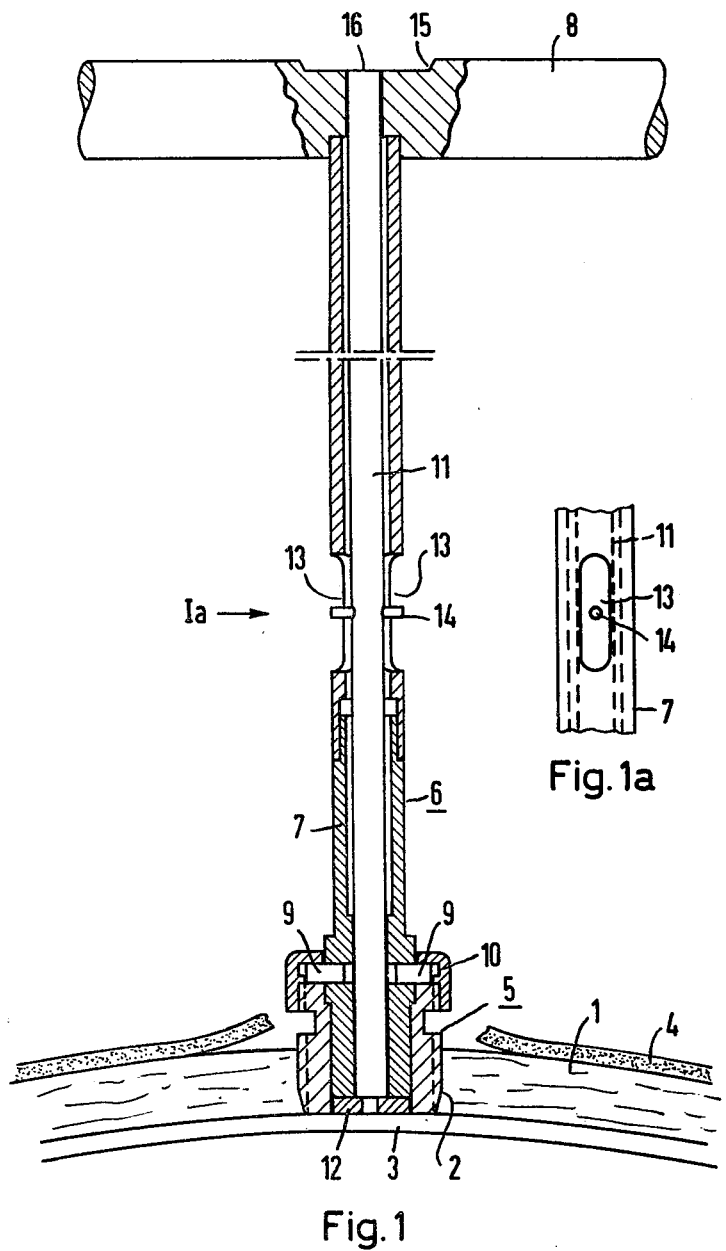
FIG. 1 shows a longitudinal section through a screwing-in instrument connected to an adapter, in the state where it is screwed into the skull.

The same instrument and adapter are represented in the figures in different stages of application and the details are therefore given the same reference numerals. Numeral 1 denotes a cranial bone of a patient with a prepared perforation 2. On the underside of the cranial bone runs the 'Dura Mater' designated by reference numeral 3 on which during pressure measurement the pressure-sensitive membrane of the pressure receptor must lie in a coplanar manner; on the top side of the cranial bone is the scalp 4 which can be closed over the adapter again after application of the pressure converter. Located in the perforation 2 of the cranial bone 1 is the adapter 5. An adapter such as described in German Utility Model No. 77 06 739.1 is preferably used as adapter 5, so it is unnecessary to describe it in detail. Connected to the adapter 5 is a pivot pin assembly 6 acting as the screwing-in instrument. The pivot pin assembly 6 includes a hollow tube 7 with a hand or screw operating grip 8 attached to the distal end and two fixing pins 9 in transverse direction at the proximal end. The proximal end of the hollow tube 7 is inserted in a form- and force-locking manner into the adapter 5 with the pins 9 engaging in corresponding recesses of configuration for rotational drive engagement of the pins 9 with the adapter 5, and is secured in such engagement by the screw cap 10. Instead of the force-locking connection by means of pins 9 and cooperating recesses, one with a polygon profile at the proximal end of the pivot pin 6 and a corresponding inside profile in the adapter 5 can be used. Inside the hollow tube 7 of the pivot pin assembly 6 there is a guided, axially displaceable pin 11. Attached to the proximal end of the pin 11 is a flat disc 12 as the abutment member. This disc 12 has the same diameter as the hollow tube 7 and fills the inside diameter of the adapter 5. At an adequate distance from the proximal end (preferably in the lower third) the hollow tube 7 has two recesses 13 on opposite sides. These recesses 13 are preferably round or oval in construction. Through the recesses 13 the position of the axially displaceable pin 11 may be observed by the operator. In this area the axially displaceable pin 11 has a transverse pin 14 with a greater length than the diameter of the tube 7. The transverse pin 14 acts, on the one hand, as limitation for the axial displacement of the pin 11 and as handle during displacement of the pin 11 for the abutment of the abutment member 12, on the 'dura mater'. On the other hand, the transverse pin 14 can also be used as a visual index mark, which is particularly clear from FIG. 1a. With a round recess 13 and the round diameter of the pin 14, the central arrangement of the pin 14 in the round recess 13 marks the exact position of the adapter 5 in flush seal with the underside of the bone. If exact data about the bone thickness, screw-in depth, etc. are to be given, it is useful to make the recess 13 oblong and to apply additional longitudinal marks to the recess 13 and/or axially displaceable pin 11. In the embodiment the pin 11 is of a length such that the end 16 of the pin 11 facing away from the abutment member seals flush with the edge of the screw grip 8 if the abutment surface of the disc 12 and the lower surface of the adapter lie in the same plane. For exact control, the hand grip 8 has a window shoulder 15 in the area of the hollow tube 7.

Figures 2, 2A:
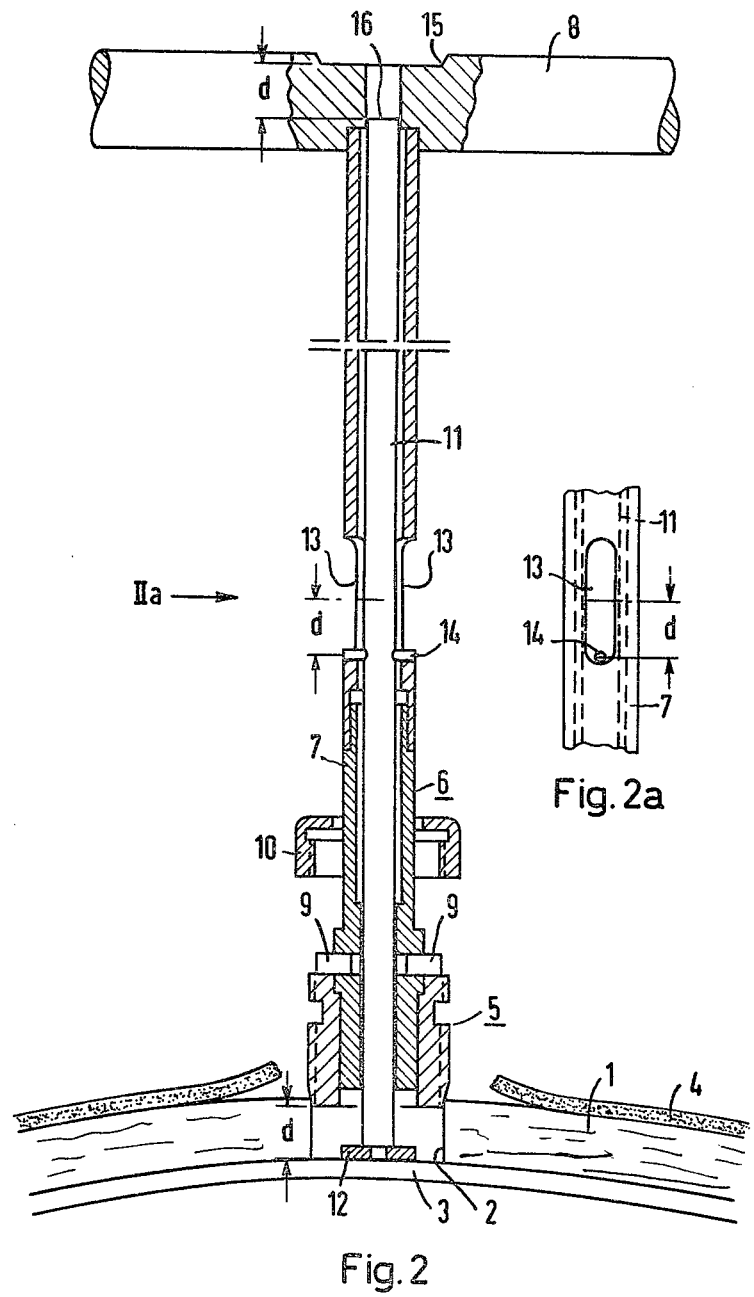

FIG. 1 shows the adapter 5 in the applied state. The proximal underside and the bone edge of the cranial bone 1 are sealed flush if application is correct. The instrument 6 may then be removed and a pressure converter inserted in its place and secured with a similar screw cap to cap 10. In FIG. 2, on the other hand, the adapter 5 and instrument 6 are represented before the screwing in operation is commenced. The adapter 5 connected to the instrument 6 is inserted with its conical end into the prepared perforation 2. The axially displaceable pin 11 is displaced by means of the transverse pin 14 in proximal direction until, as shown in FIG. 2, the disc 12 lies with its lower surface on the 'dura mater'. The pin 11 then has been displaced axially by the depth d, whereby the edges of the window shoulder 15 and the end 16 of the pin 11 are offset by the distance d. In this position the transverse pin 14 is similarly at a distance d from the center of the recess 13, for instance at the outside end of the recess 13. The screw cap 10 for fixing the instrument 6 in position is represented in FIG. 2 in the state where it is not yet screwed on. After the screw instrument 6 has been fixed by means of the screw cap 10, the screwing-in operation of the adapter 5 may begin. During the screwing-in operation the hollow tube 7 and the pin 11 are displaced relative to one another. After the adapter 5 has been screwed in by the distance d the window shoulder 15 and the end 16 of the pin seal flush as shown in FIG. 1. The adapter is then applied accurately (according to FIG. 1). In this position the transverse pin 14 is again central in the recess 13 as shown in FIG. 1a.

By way of further example, the axially displaceable element 11 may have a transverse linear index mark, for example at the midpoint of each of the longitudinal surface portions of element 11 which are visible through the slots in tube 7, as seen in FIG. 2a. For cooperating with this index mark, uniformly longitudinally spaced transversely extending linear markings could be provided at each side of each slot. The final position would be indicated by markings on the tube 7 at a distance d above the mid position indicated in FIG. 2a. Such final position markings would then line up with the index mark on element 11 in the final position of FIGS. 1, 1a.

It will be apparent that many modifications and variations may be effected without departing from the scope of the novel concepts and teachings of the present invention.

I claim as my inventions:
1. The method of inserting a hollow adapter into an opening in a human cranium, which comprises
    (a) temporarily engaging the adapter with one axial end of a hollow tube (7) for joint rotation, and with an interior space of the hollow tube aligned with a hollow space of the adapter, and with a gauge element (11) extending through the aligned interior space and hollow space and terminating in a disk abutment member, so that the adapter and hollow tube can advance axially relative to the gauge element,
    (b) positioning the gauge element axially in the tube such that the disk abutment member rests against the dura mater (3) at the opening in the human cranium,
    (c) drivingly rotating the tube (7) to rotate the adapter and drive the same into the opening while the disk abutment member continues to rest on the dura mater (3),
    (d) continuing the driving of the adapter into the opening until gauging indicia on the gauge element and on the hollow tube indicate that the adapter is flush with the engaging face of the disk abutment member which engages the dura mater, and
    (e) thereafter disengaging the hollow tube from the adapter and removing the hollow tube and gauge element from the opening to expose the dura mater for application of a pressure converter to be inserted into the hollow space of the adapter.

* * * * *